United States Patent [19]
Young

[11] Patent Number: 5,656,015
[45] Date of Patent: Aug. 12, 1997

[54] ULTRASONIC THERAPEUTIC SYSTEM

[75] Inventor: Michael John Radley Young, Ashburton, United Kingdom

[73] Assignee: Orthosonics, Ltd., Ashburton, United Kingdom

[21] Appl. No.: 425,139

[22] Filed: Apr. 19, 1995

[30] Foreign Application Priority Data

Apr. 30, 1994 [GB] United Kingdom .................. 9408668

[51] Int. Cl.⁶ .................................................. A61B 19/00
[52] U.S. Cl. ............................................. 601/2; 128/660.03
[58] Field of Search .................. 601/2, 3, 4; 128/660.03; 607/97; 310/311

[56] References Cited

U.S. PATENT DOCUMENTS

| | | |
|---|---|---|
| 4,359,726 | 11/1982 | Lewiner et al. |
| 4,823,042 | 4/1989 | Coffey . |
| 5,457,863 | 10/1995 | Thomas, III et al. |

FOREIGN PATENT DOCUMENTS

| | | |
|---|---|---|
| A0538241 | 6/1989 | European Pat. Off. |
| A0465870 | 6/1991 | European Pat. Off. |
| 3033598 | 4/1982 | Germany . |
| A3616274 | 5/1986 | Germany . |
| C302201 | 12/1954 | Switzerland . |
| 8911163 | 11/1989 | WIPO . |
| WO-A9316652 | 9/1993 | WIPO . |
| WO-A9503744 | 2/1995 | WIPO . |

OTHER PUBLICATIONS

Proc. Ann. Int. Conf. IEEE Engineering in Medicine Soc., vol. 15, 28 Oct. 1993, pp. 196–197, XP 000436716, Hartov, "Intraoperative Ultrasound Hyperthermia System".

Primary Examiner—Marvin M. Lateef
Assistant Examiner—Shawna J. Shaw
Attorney, Agent, or Firm—Hopgood, Calimafde, Kalil & Judlowe

[57] ABSTRACT

In a preferred embodiment, the invention provides a plurality of spaced ultrasonic piezoelectric transducers, which may be so fixed to and around an afflicted area of a patient as to enable their sequential or interlaced excitation, whereby the afflicted area of the patient can be excited from different aspects, so that ultrasonic energy is not permitted to enter the body from any single point on a continuous-wave basis. Each transducer delivers its ultrasonic energy via a body of material having a wave impedance that substantially matches the wave impedance of human soft tissue, thereby avoiding or minimizing the annoyance of a mismatched entry into the patient's body. The net result is for the patient to derive the therapeutic benefits of a moving applicator, without any physical displacement of one with respect to any other of the plural spaced transducers. Various embodiments and an illustrative plurality of different excitation sequences are described.

25 Claims, 6 Drawing Sheets

ULTRASONIC THERAPEUTIC SYSTEM

BACKGROUND OF THE INVENTION

The present invention relates to a therapeutic system utilizing ultrasonic vibrations. More particularly, but not exclusively, it relates to a system which can be attached to a living body to be treated and remain there for a period of several treatments, if so desired or required.

It is known from our International application number PCT/GB93/00374 to treat body tissue by means of low frequency ultrasonic vibrations. In said application, the vibrations are applied through a treatment head which is moved around and across the area to be treated. If it is not so moved, heat may be generated in the tissue at the point where the head is stationary. Hence, use of the device described in said International application requires a certain degree of skill in the user and continuous attention during treatment.

Conditions susceptible to treatment using ultrasonic vibration at low frequency include muscle spasms, skin ulceration, sprains, haematoma and the like. One particular problem is varicose leg ulcers which can require protracted treatment over a period of months or even years, involving specialist nursing attention. Given the frequency of such conditions, it is not always possible to provide enough experienced staff to carry out the treatment, and patients may therefore suffer.

BRIEF STATEMENT OF THE INVENTION

It is an object of the present invention to provide therapeutic apparatus which can be attached to the body to be treated and remain there for a course of several or many treatments, which may be performed at predetermined intervals. Once the apparatus is attached, it should work automatically to scan the area to be treated with a plurality of sequential ultrasonic pulses, thereby materially reducing the duty cycle at any single location and avoiding any local heating of the body, and thereby also more broadly and volumetrically distributing a desired therapy, without standing-wave development in the treated zone of the patient.

A preferred embodiment of the invention achieves this object by providing in a single device a plurality of spaced ultrasonic piezoelectric transducers, which may be so fixed to and around an afflicted area of a patient as to enable their sequential or interlaced excitation, whereby the afflicted area of the patient can be excited from different aspects, so that ultrasonic energy is not permitted to enter the body from any single point on a continuous-wave basis. Preferably, each transducer delivers its ultrasonic energy via a body of material having a wave impedance that substantially matches the wave impedance of human soft tissue, thereby avoiding or minimizing the annoyance of a mismatched entry into the patient's body. The net result is for the patient to derive the therapeutic benefits of a moving applicator, without any physical displacement of one with respect to any other of the plural spaced transducers. Various embodiments and an illustrative plurality of different excitation sequences are described.

BRIEF DESCRIPTION OF THE DRAWINGS

The invention will be described in detail in conjunction with the accompanying drawings, in which.

DETAILED DESCRIPTION

Figure 1:
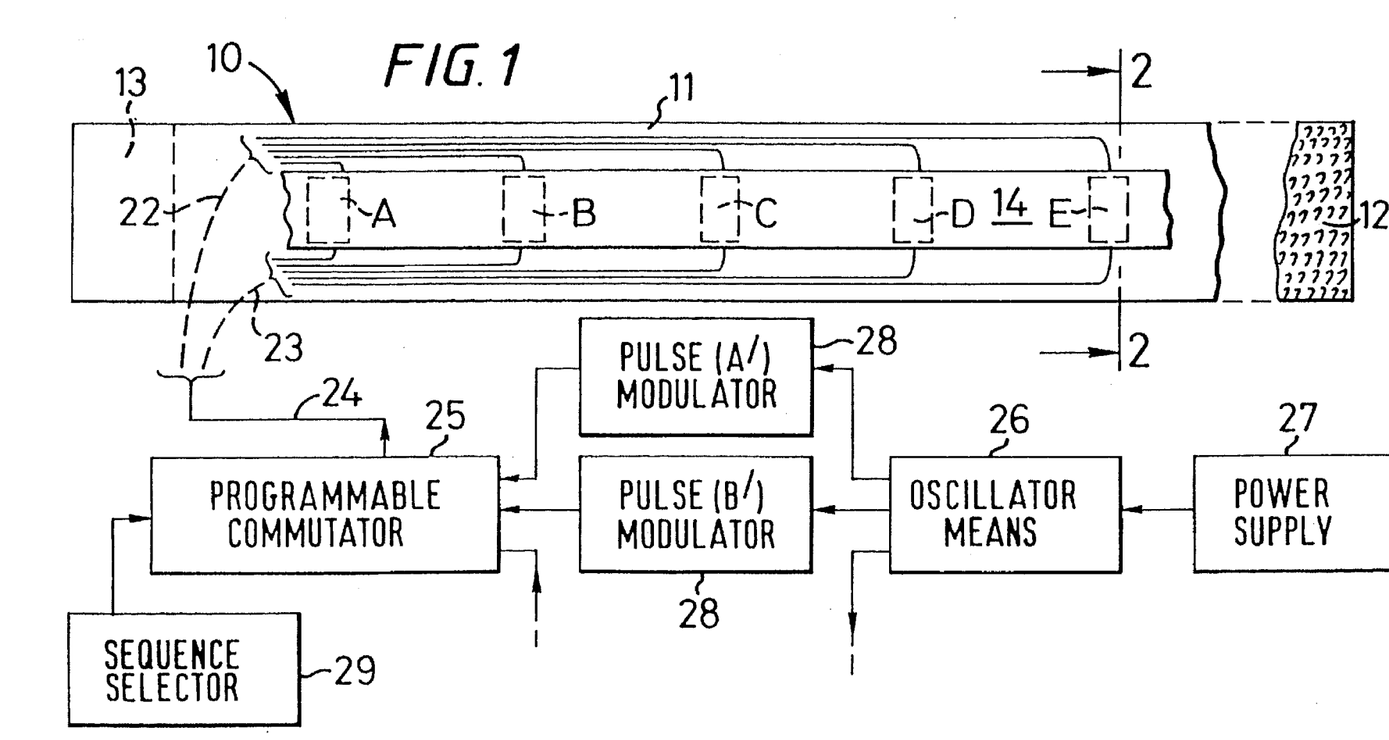
FIG. 1 is a simplified plan view of the active underside or inner side of an elongate bandage embodying the invention and adapted for circumferential application around a limb or other body part of a patient.

FIG. 1 illustrates a preferred embodiment of the invention, in the form of an elongate bandage 10 having a base 11 of conventional bandage material, for example, material used in a so-called ace bandage, with means such as removably engageable hook-and-loop patches 12, 13 at its respective ends, to permit selectively tensed retention around an afflicted limb of a patient. An elongate flexible strip 14 of plastics material, having an acoustic wave impedance which is close to or which substantially matches the acoustic wave impedance of soft living tissue, is carried on the underside of the bandage material 11, and a plurality of like piezoelectric transducer elements A B, C D, E is shown mounted to the strip 14 at longitudinally spaced locations. It is to be understood from FIG. 2 that each transducer element is carried between the bandage material and the adjacent surface of the plastic impedance-matching strip 14, so that the opposite surface of strip 14 can be applied to and retained against soft tissue (skin) of the patient, near or adjacent to the subcutaneous region to be treated. The material of strip 14 may suitably be acetal, or polypropylene or polycarbonate, or a reinforced laminate using carbon or glass fibre elements in a suitable resin matrix.

Figure 2:
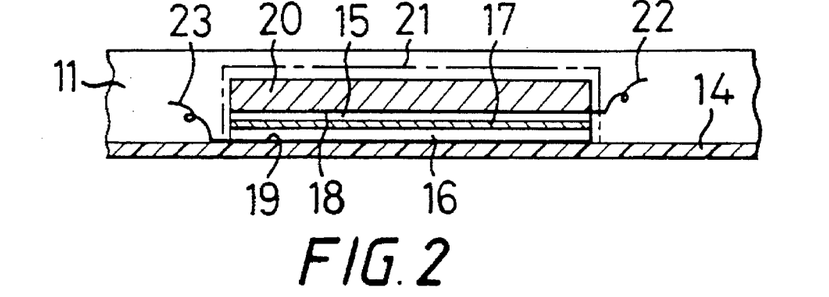
FIG. 2 is an enlarged sectional view of a transducer element, taken at 2—2 in FIG. 1.

More particularly, each transducer element is shown to comprise a sandwich construction wherein separate piezoelectric layers 15, 16 are bonded to a central conductive plate 17, and wherein outer conductive-foil electrodes 18, 19 cover the respective outer surfaces of the piezoelectric layers 15, 16. A backing element 20 is bonded (with foil 18) to piezoelectric layer 15, and the remaining or active face of layer 16 is (with foil 19) bonded to the plastic strip 14. A protective jacket or coating 21 of acoustic pressure-release material, such as a gas or air-expanded elastomeric foam, covers the backing element 20 and preferably also all sides of each transducer element, except of course the active face, which is adapted to be acoustically coupled to the patient, via plastic strip 14 and its direct contact with skin.

FIG. 1 further shows the provision of individual leads (collectively designated 22) to all first-electrode foils 18 of the respective transducer elements, as well as individual leads (collectively designated 23) to all second-electrode foils 18; a grounding connection to all plates 17 is not shown specifically but will be understood to be one of the conductors of a single flexible cable 24 to the output of electrical commutator means 25 to drive the respective transducer elements. All such leads may be provided by metal-deposition on the inner surface of the impedance-matching plastic strip 14, using printed-circuit techniques.

As shown, oscillator means 26 fed by suitable power-supply means 27, provides separate outputs of a given low-frequency ultrasonic frequency to each of a succession of like but separately characterized pulse modulators 28, each of which will be understood to provide separate excitation via commutator means to a different one of the transducer elements, as suggested by primed parenthetic notation in FIG. 1, for each of the modulators 28.

Figure 5:
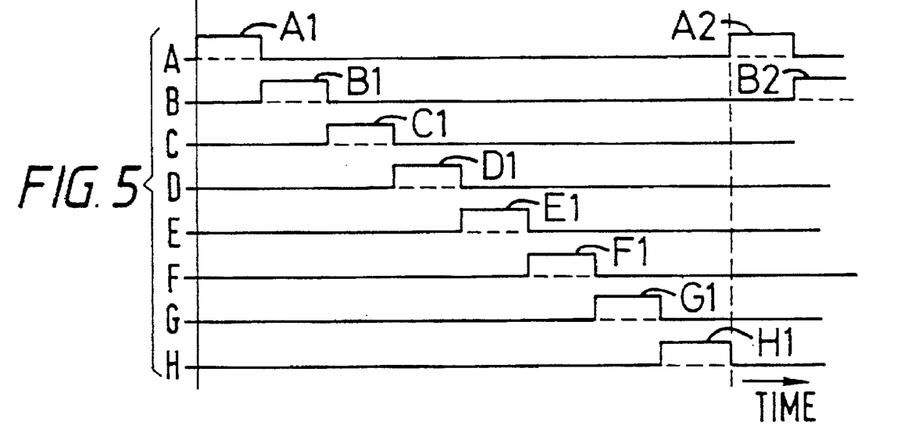
FIG. 5 is a simple graphical display, for a single timed cycle to show a first illustrative timed sequence of transducer excitation.

More specifically, further reference is made to FIG. 5, which depicts a commutation-cycling program for an array of eight transducer elements (A, B, C . . . H) of the nature described in connection with FIGS. 1 and 2. According to FIG. 5, each pulse modulator 28 provides identically the same envelope of pulse modulation for the low-frequency ultrasonic output from oscillator means 26, but the respective outputs of modulators 28 are in a predetermined time sequence to the respective transducers. Thus, a first cycle of pulse modulation, in FIG. 5, begins with a burst (A1) of ultrasonic excitation for transducer A alone, followed in the same first cycle with a like burst (B1) of ultrasonic excitation for transducer B alone. The same first cycle proceeds in stepped sequence, for each of the pulse modulators 28 and their corresponding transducers, until cycle completion at termination of the last burst of ultrasonic excitation of the last transducer (H), whereupon the next cycle commences with burst A2 to the first transducer A.

Referring again to FIG. 1, it is indicated at 29 that sequence selection is an available option, whereby to selectively alter the sequence of transducer excitation by the respective outputs of pulse modulators 28. Thus, for example, pursuant to a selection at 29 (other than the straight-sequential pattern described in connection with FIG. 5), the burst A1 may start a different cycle program with excitation of transducer A, the same to be immediately followed with burst B1 connected for excitation of transducer D, to be then immediately followed by burst C1 delivered to transducer B, and so on in an alternating pattern of three transducers forward, interlaced with a pattern of two transducers backward, to produce the following sequence of operating the eight transducers—A, D, B, E, C, F, D, G, E, H, F, A, G, B, H, C, at which point, a second identical cycle begins with A, D excitations.

Figure 6:
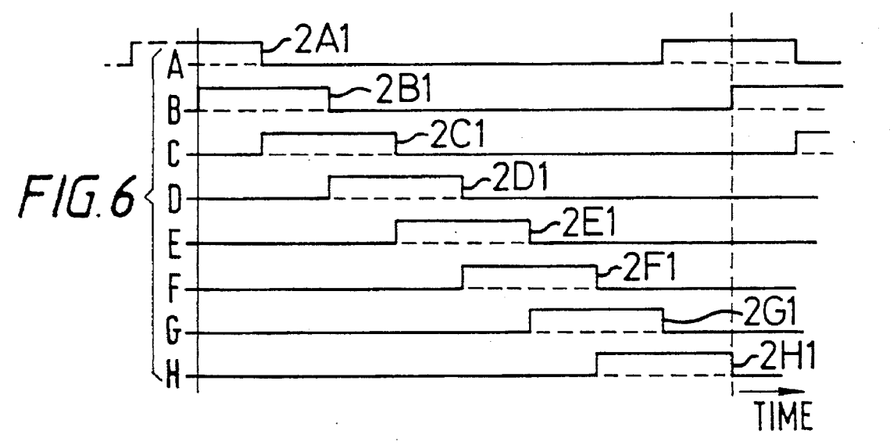
FIG. 6 is a display similar to FIG. 5 to show a second illustrative timed sequence.

FIG. 6 serves further to illustrate selection of a sequence at 29 to produce a succession of bursts of ultrasonic energy from transducers A, B . . . H, wherein all bursts are twice the duration of bursts pursuant to FIG. 5, and wherein there is such overlap of bursts that two different transducers are irradiating at all times. Thus, the first burst 2A1 is the second half of what would otherwise be a double-length pulse-modulating envelope attributable to pulse modulator A' in FIG. 1, and this second half of the burst 2A1 is coincident with the first half of the burst 2B1, attributable to pulse modulator B'. If the transducers A, B . . . H are thus driven in progressive overlap, it follows that affected soft tissue in an afflicted zone can "see" the transfer of therapeutic ultrasonic-energy as a "smoothed" delivery, in that two transducers are being excited at any given time in the cycle. Again, it should go without saying that the excitation of transducers need not be one of progressive overlap for a succession of adjacent transducers. Thus, for example, the pattern of FIG. 6 may be applied, if so selected at 29, to produce the following sequence of operating the eight transducers: A lapped with E, E lapped with B, B lapped with F, F lapped with C, C lapped with G, G lapped with D, and D lapped with H, with M lapped with A to complete the cycle.

In the further illustrative program of FIG. 7, again selectable at 29, pulse-modulated bursts are as described for FIG. 5, except that two cycles of pulse modulations produce identical-length bursts of ultrasonic energy with the same cycle period as described for FIGS. 5 and 6. This situation is recognized by notation A11 and A12 in the first double cycle, followed by A21 and (graph space permitting) A22 in the second double cycle.

Figure 8:
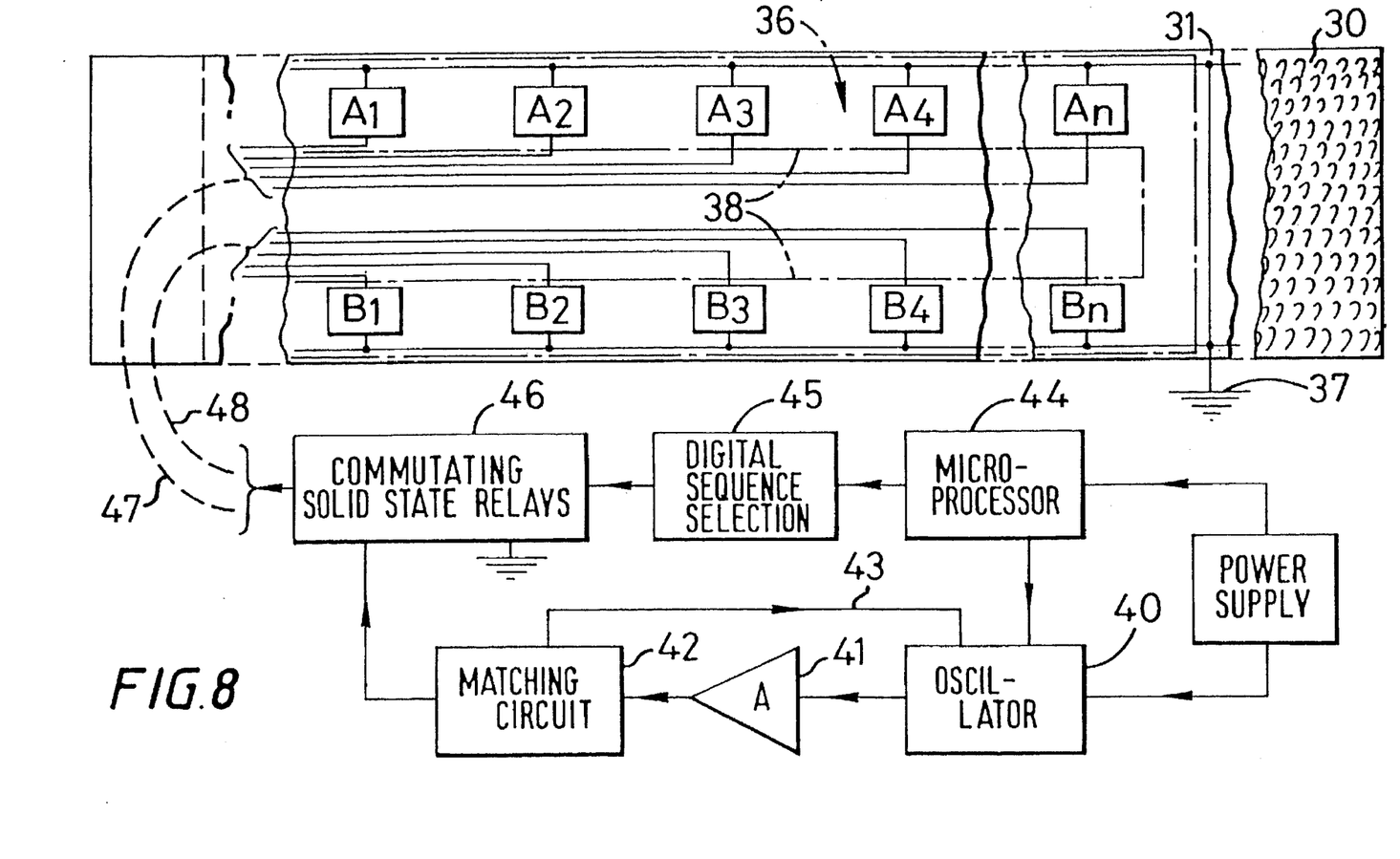
FIG. 8 is a view similar to FIG. 1, to show another embodiment.
Figure 9:
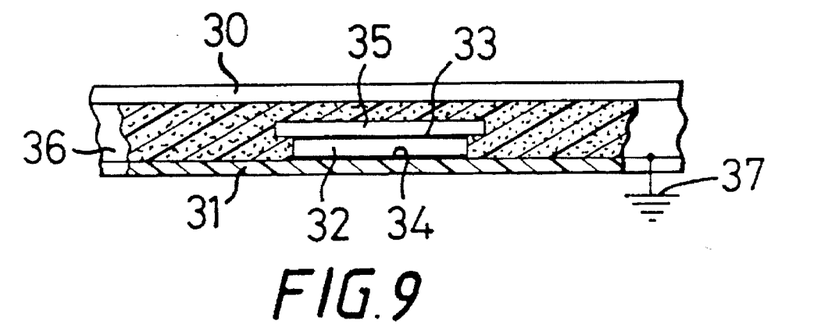
FIG. 9 is a fragmentary sectional view similar to that of FIG. 2 but applicable to one of the transducer elements of FIG. 8.

In the embodiment of FIGS. 8 and 9, two longitudinal successions of transducer elements $A_1, A_2 \ldots A_n$, and $B_1, B_2 \ldots B_n$, are mounted in transversely spaced array to and between a base 30 of bandage material and a single plastic strip 31; and each transducer element comprises a single layer 32 of piezoelectric material such as PZT having a first foil electrode 33 on its upper face and a second foil electrode 34 on its lower face. A backing plate 35 and foil electrode 33 are bonded to the upper face of piezo layer 32; and foil electrode 34, together with the lower face of the piezo layer 32, is bonded to strip 31. It is particularly helpful if the upper face of strip 31 is metalized, as suggested at 36 in FIG. 9, so that this metalized surface may serve as the earth (or ground) terminal for all transducer elements, noting the ground symbolism at 37 in each of FIGS. 8 and 9. A separate elongate flexible substrate of insulating material, suggested in FIG. 8 by phantom outline 38, may be bonded to strip 31, bearing printed-circuit lead connections for the electrically driven upper foil electrodes 33; alternatively, the metalized layer 36 of strip 31 may be limited to an annular or horseshoe configuration serving all lower-foil transducer electrodes, leaving a space equivalent to phantom outline 38 therebetween, in which case the printed-circuit lead connection may be accommodated within said annular or horseshoe configuration, thus avoiding any need for a separate ply of substrate, dictated only to assure insulation from ground potential.

Figure 7:
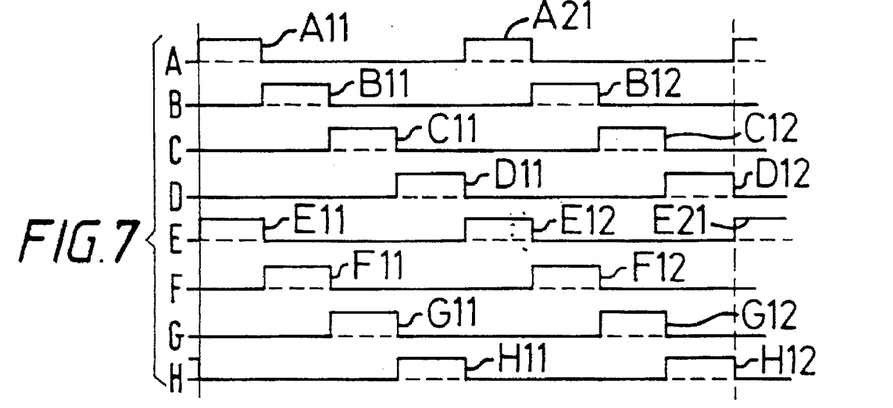
FIG. 7 is another display as in FIG. 5, for a third illustrative timed sequence.

The supply of signal voltages pursuant to a predetermined sequence pattern in FIG. 8 is shown to rely upon an oscillator 40 in a phase-locked loop which also includes an amplifier 41 and a matching circuit 42, with a feedback return connection 43 to the oscillator. Basic control is via a microprocessor 44, with connections to oscillator 40 and to a digital means 45 of sequence selection for operation of commutating means 46. The legend at 46 indicates preference that commutating switch operations at 46 shall be via solid-state relays, serving to channel the output of the phase-locked loop into a preselected succession of the transducers $A_1, A_2 \ldots A_n$ and $B_1, B_2 \ldots B_n$, via flexible cables suggested at 47, 48. The variety of excitation patterns described in connection with FIGS. 5, 6 and 7 is equally applicable in illustration of the variety achievable with the apparatus of FIGS. 8 and 9, and of course a wider swath of excitation patterns is available from the spaced parallel arrays of transducers $A_1, A_2 \ldots A_n$ and $B_1, B_2 \ldots B_n$.

Figure 10:
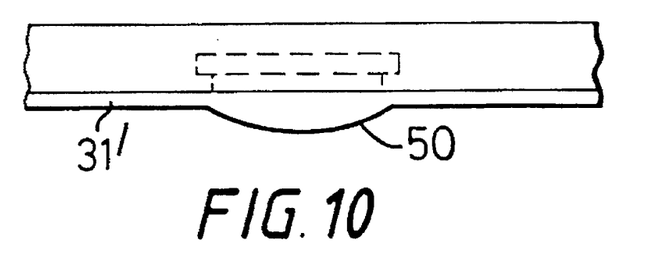
FIG. 10 is a view in side elevation of a transducer element representing a modification from the element of FIG. 9.

FIG. 10 illustrates a modification of the impedance-matching strip 31 of FIG. 9, wherein, at each transducer mount to strip 31', the lower (skin-contacting) surface features a convex bulge 50 which may be either a truncation of a sphere or a truncation of a cylinder, and which provides not only enhanced probability of effective transfer of ultrasonic energy at local contact with soft tissue, but also a greater divergent propagation of such energy within the affected region of the patient's body.

Figure 3:
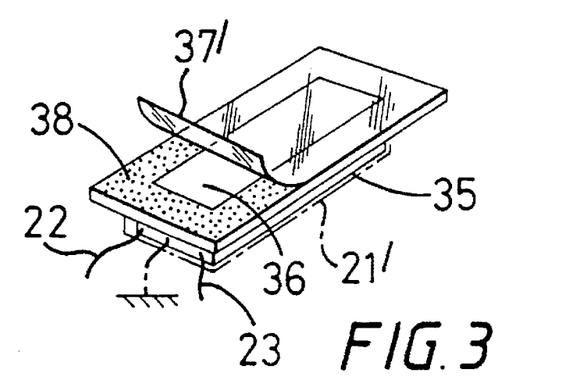
FIG. 3 is a perspective view of a single transducer element, which may be one of those in the bandage embodiment of FIG. 1.
Figure 4:
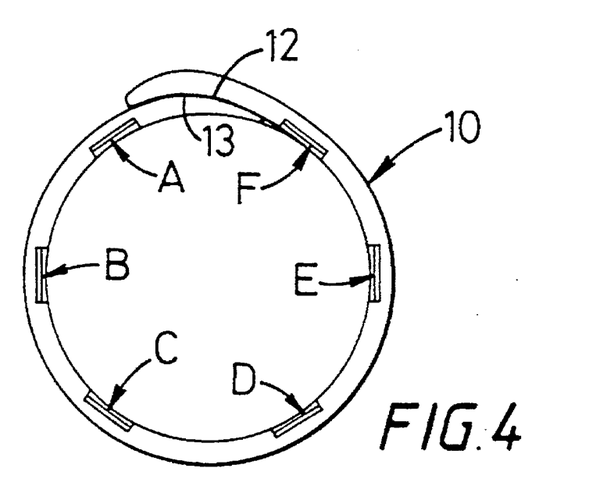
FIG. 4 is a simplified side or end view of a completed bandage of the nature of FIG. 1, as the same may appear as an endless wrap around a human limb.

The invention has been described in detail for relatively specific wrapped-bandage embodiments, but a variety of embodiments is contemplated. For example, a basic transducer element 35 as shown in FIG. 3 lends itself as a separate article of commerce, salable alone, or in combination with other elements as so to provide the professional therapist with a kit to enable him to design his multiple-element system to serve special purpose applications unique to the problem of each patient. Such a kit will be understood to comprise a plurality of transducer elements as in FIG. 3, plus one or sheets or precut configurations of impedance-matching plastic material 14, which is to serve one or more particular purposes, along with bandage, tape, adhesive and wiring to permit connection to electronic excitation apparatus of the nature suggested in FIG. 1. Specifically, as to the element 35 of FIG. 3, for example, it is seen that the active face 36 of the transducer is precoated with a suitable adhesive that is protected by a peel-off release strip 37', in readiness for direct assembly to an impedance-matching strip 14 or other configuration of such material. In FIG. 3, a peripheral flange 38 of a coating 21' of acoustic pressure-release material encases all but the active face 36 of the transducer element, and flange 38 is precoated with pressure-sensitive adhesive for better assurance of transducer location in a given selected area of the impedance-matching strip or layer 14. To complete the description of FIG. 3, three separate insulated leads emerge from the pressure-release enclosure 21' for connection to excitation electrodes and the grounding plate 17 of the transducer. By analogy, an individual transducer element for the system of FIG. 8, may have the same appearance as that of FIG. 3, except that only one or at most two leads is required, depending upon whether the impedance-matching material to be used with the element is or is not conductively coated to serve the grounding purpose described in connection with FIGS. 8 and 9.

Figure 11:
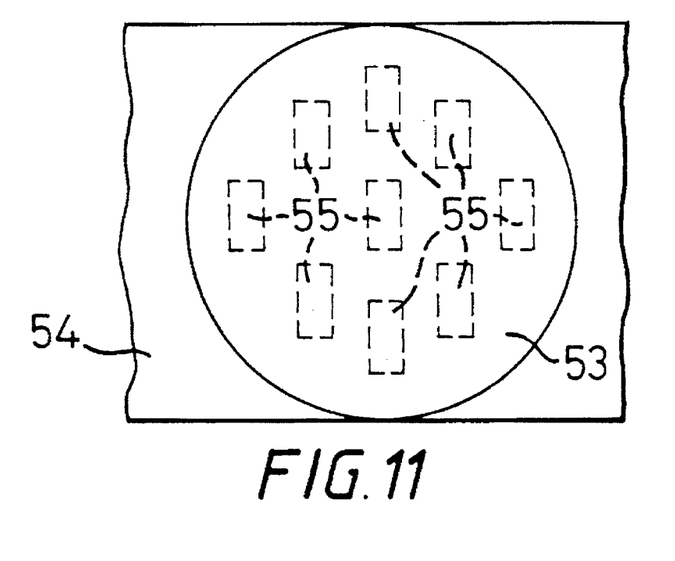
FIG. 11 is a view of the active underside or inner side of another multiple-element transducer device of the invention.

FIG. 11 illustrates that the configuration of the flexible area of impedance-matching plastic material 53 may be more two-dimensional than is implied for the embodiment of FIG. 1. In FIG. 11, the material 53 is generally circular, in the nature of a patch mounted to adhesive tape or bandage material 54, for retained attachment to a selected part of the body of the patient. As shown, a two-dimensional array of transducer elements 55, as at 35 in FIG. 3, is distributed in active-face (36) bonded assembly to material 53, between material 53 and the tape or bandage material 54.

Figure 12:
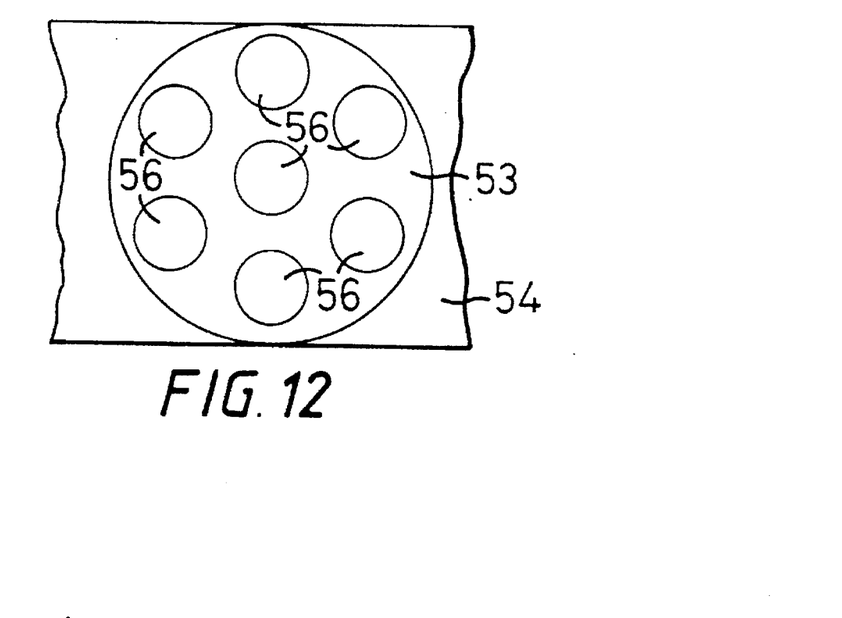
FIG. 12 is a view similar to FIG. 11 for a further modification.

Although shown as of rectangular outline, in either a single-layer or a double-layer piezoelectric sandwich construction, it will be understood that elemental transducers as described for use with excitation/driver apparatus of FIG. 1 or of FIG. 8, may be of single or double piezoelectric circular-disc configuration, thus enabling the device of FIG. 12 to be a distributed array of circular disc transducer elements 56, with their individual active faces bonded to impedance-matching material 53, between material 53 and the tape or bandage material 54.

For all disclosed embodiments of the invention, it is contemplated that the low frequency of ultrasonic excitation shall be in the range of 20 to 120 kHz, with a preference stated for approximately 45 kHz, plus or minus 5 kHz. At any given time, energy level delivered to a patient's body should be in the range of 30 to 100 milliwatts/cm$^2$, and preferably about 75 milliwatts/cm$^2$. The pulsing envelope should be sufficiently short (e.g. 10 seconds or less) for each pulse delivery to avoid establishment of a standing-wave condition within the body. An acceptable approach to wave-impedance match to the wave impedance of human soft tissue, namely, $1.65 \times 10^6$ kg m$^{-2}$ sec$^{-1}$, is available for use of acetal material at 14 and 40, in which case the wave impedance of such material is $1.86 \times 10^6$ Kg m$^{-2}$ sec$^{-1}$. In other words, present preference is that the approach to impedance match with human soft tissue shall be in the range of 1 to 1.2 times the wave impedance of human soft tissue.

Although the invention has been described for the area of impedance-matching material (e.g. at 14, 31 and at 53) to substantially exceed the active-face area of each individual transducer element, it will be understood that each transducer element may be in fully bonded assembly to its own active transducer face, and of substantially matching area, as suggested for the case of the elemental unit 50 of FIG. 10. Also, it will be understood that an elongate strip (14, 31) or patch (53) may be preformed with additional thickness local to each transducer element mounted thereto, creating a layer (31') surface which is somewhat bulging and bulbous at 50, the locale of soft skin application, thus in certain cases further promoting the effectiveness of acoustic coupling to the patient's body.

The exact mechanism of operation of multiple-element arrays as in FIGS. 1 and 8 is not at present fully understood, but the possibility exists that two adjacent and spaced transducer elements (A, B in FIG. 1; or $A_1, A_2$ in FIG. 8, or $A_1, B_1$ in FIG. 8), being bonded to the same impedance-matching strip 14 (or 30) may, if excited in cophasal relation, be a stimulant of flexural-wave development in strip 14 (or 30) such that a greater amplitude of energy transfer into body tissue will occur between the involved adjacent transducer elements. This possibility is illustrated by the wave diagram of FIG. for the case of the adjacent transducers 60, 61, 62 of FIG. 13, wherein the impedance-matching strip 63 is shown as a consolidation of laminations 64, 65 at least one of which may for example have the described printed circuit conductors, and wherein laminate consolidation into a single strip affords protection to the conductors, within the laminated interface. A layer 67 of pressure-release material, such as a foamed elastomeric, will be seen to coat the backside of all transducers, as well as the backside of strip 14 in regions between adjacent individual transducer elements.

Figure 13:
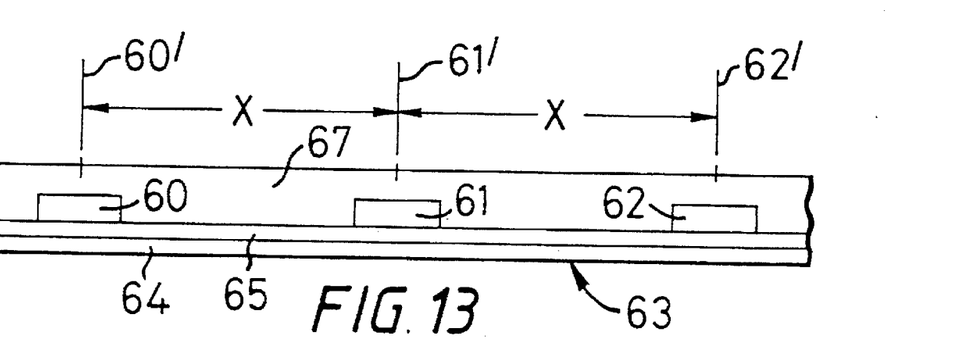
FIG. 13 is a simplified side view of three successive transducer elements mounted to a two-ply laminate for direct application to a body.
Figure 14:
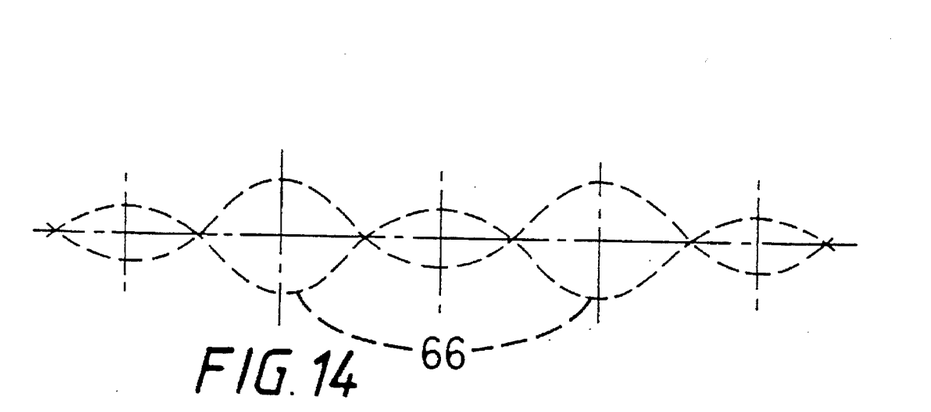
FIG. 14 is a graphical display of transverse wave form development, related to the longitudinal scale of FIG. 13.

FIGS. 13 and 14 are drawn to the same scale of their center-to-center spacing of transducer elements, in order to show that the principal energy transfer to the body may occur at region 66 midway between the respective axes 60', 61', 62' of individual transducer output, provided that, for example, the spacing X between axes 60', 61', 62' is an integral multiple of the wavelength of transverse propagation in the coupling laminate 64, 65.

In any of the described embodiments, it is noted that shape and style of transducer elements are not critical factors. However, for a bandage-type assembly, as in FIGS. 1 and 8, the overall width dimension can be a somewhat limiting factor for wrap-around flexibility and assured coupling of ultrasonic-energy delivered to circumferentially spaced locations on a body. A preference is thus indicated that the overall bandage width be in the range of 1.5 to 2.5 inches, in which case, circular piezoelectric elements (e.g. 56 in FIG. 12), if arrayed as in FIG. 1, may be in the order of 1-inch diameter or less; and if arrayed as in FIG. 8, such circular elements may be in the order of ½-inch diameter or more. Similarly, for a rectangular or square configuration, the long-side dimension may be of 1-inch or less in the FIG. 1 array (e.g. 0.5 inch by 1-inch, or as much as 1-inch square), and in the FIG. 8 array, the transducer elements may be 0.5 inch by 0.5 inch or more).

What is claimed is:

1. An ultrasonic therapeutic device, comprising a flexible substrate material adapted for retained application to a part of a living body, said substrate material having an inner face carrying two or more piezoelectric transducer elements in spaced array, an impedance matching layer bonded to each of said elements for direct application to the body, and flexible conductor means which at least in part comprise printed circuitry carried by said impedance-matching layer, said flexible conductor means being associated individually with one to the exclusion of another of said elements for individually exciting said elements for irradiation into the body via said impedance-matching layer, said impedance-matching layer being a composite of two laminations of impedance-matching material, with said printed circuitry on one surface of one of said laminations, the printed-circuitry surface being at the interface between the consolidated laminations, the impedance of said impedance-matching layer being substantially that of soft living tissue.

2. The device of claim 1, in which said impedance-matching layer is an elongate strip, with said piezoelectric elements in spaced array along said strip.

3. The device of claim 1, in which said impedance-matching layer is a separate assembled component of each piezoelectric element.

4. The device of claim 2, in which said array is a single-dimension array, with said elements in longitudinally spaced relation.

5. The device of claim 2, in which said array is a two-dimensional array, with said elements in longitudinally spaced and transversely spaced array.

6. The device of claim 1, in which each piezoelectric transducer element is rectangular and includes a rectangular backing plate.

7. The device of claim 1, in which each piezoelectric transducer element is circular and includes a circular backing member.

8. The device of claim 5, in which said impedance-matching layer is an elongate strip, and said two-dimensional array comprises first and second transversely spaced alignments of longitudinally spaced transducer elements mounted to said elongate strip.

9. The device of claim 5, in which said impedance-matching layer is generally circular, and said two-dimensional array comprises transducer elements in angularly spaced distribution within the circumference of said impedance-matching layer.

10. An ultrasonic therapeutic device, comprising a flexible substrate material adapted for retained application to a part of a living body, said substrate material having an inner face carrying two or more piezoelectric transducer elements in spaced array, an impedance matching layer bonded to each of said elements for direct application to the body, flexible conductor means associated individually with one to the exclusion of another of said elements for individually exciting said elements for irradiation into the body via said impedance-matching layer, the impedance of said impedance-matching layer being substantially that of soft living tissue, and a pressure-release layer covering at least the backside of each transducer element.

11. An ultrasonic therapeutic device, comprising a flexible substrate material adapted for retained application to a part of a living body, said substrate material having an inner face carrying two or more piezoelectric transducer elements in spaced array, an impedance matching layer bonded to each of said elements for direct application to the body, said impedance-matching layer is an elongate strip, with said piezoelectric elements in spaced array along said strip, flexible conductor means associated individually with one to the exclusion of another of said elements for individually exciting said elements for irradiation into the body via said impedance-matching layer, the impedance of said impedance-matching layer being substantially that of soft living tissue, and a pressure-release layer covering the backside of each transducer element as well as the backside of said impedance-matching layer in spaces between adjacent transducer elements.

12. An ultrasonic therapeutic device, comprising a flexible substrate material adapted for retained application to a part of a living body, said substrate material having an inner face carrying two or more piezoelectric transducer elements in spaced array, an impedance matching layer bonded to each of said elements for direct application to the body, flexible conductor means associated individually with one to the exclusion of another of said elements for individually exciting said elements for irradiation into the body via said impedance-matching layer, the impedance of said impedance-matching layer being substantially that of soft living tissue, said impedance-matching layer having (a) a flat surface in bonded relation to each transducer element and (b) an irradiating opposite surface having a separate convexly contoured profile in register with each individual transducer element.

13. The device of claim 1, in which said conductor means for at least two adjacent transducer elements is connected for concurrent excitation of said adjacent transducer elements.

14. The device of claim 10, in which said flexible conductor means at least in part comprises printed circuitry carried by said impedance-matching layer.

15. The device of claim 10, in which said impedance-matching layer is an elongate strip, with said piezoelectric elements in spaced array along said strip.

16. The device of claim 10, in which said impedance-matching layer is a separate assembled component of each piezoelectric element.

17. The device of claim 15, in which said array is a single-dimension array, with said elements in longitudinally spaced relation.

18. The device of claim 15, in which said array is a two-dimensional array, with said elements in longitudinally spaced and transversely spaced array.

19. The device of claim 10, in which each piezoelectric transducer element is rectangular and includes a rectangular backing plate.

20. The device of claim 10, in which each piezoelectric transducer element is circular and includes a circular backing member.

21. The device of claim 18, in which said impedance-matching layer is an elongate strip, and said two-dimensional array comprises first and second transversely spaced alignments of longitudinally spaced transducer elements mounted to said elongate strip.

22. The device of claim 18, in which said impedance-matching layer is generally circular, and said two-dimensional array comprises transducer elements in angularly spaced distribution within the circumference of said impedance-matching layer.

23. The device of claim 10, in which said conductor means for at least two adjacent transducer elements is connected for concurrent excitation of said adjacent transducer elements.

24. The device of claim 2, in which the respective longitudinal ends of said strip are detachably securable to complete a peripheral application of said impedance-matching layer to a body member.

25. The device of claim 2, in which the respective longitudinal ends of said strip are detachably securable to complete a peripheral application of said impedance-matching layer to a body member.

* * * * *

UNITED STATES PATENT AND TRADEMARK OFFICE
CERTIFICATE OF CORRECTION

PATENT NO.   : 5,656,015
DATED        : August 12, 1997
INVENTOR(S)  : Michael John Radley YOUNG It is certified that error appears in the above-indentified patent and that said Letters Patent is hereby corrected as shown below:

Column 2, line 50;     after "transducer elements"
                       delete "AB, CD, E"
                       and insert therefor --A, B, C, D, E--

Column 4, line 17;     before "lapped with A"
                       delete "M" and insert therefor --H--

Signed and Sealed this

Twelfth Day of May, 1998

Attest:

BRUCE LEHMAN

*Attesting Officer*            *Commissioner of Patents and Trademarks*